US005827429A

United States Patent [19]

Ruschke et al.

[11] Patent Number: 5,827,429

[45] Date of Patent: Oct. 27, 1998

[54] INTRAVENOUS FILTER DEVICE

[75] Inventors: Ricky R. Ruschke, McHenry; John A. Leahey, Woodstock, both of Ill.

[73] Assignee: Filtertek Inc., Hebron, Ill.

[21] Appl. No.: 588,231

[22] Filed: Jan. 18, 1996

[51] Int. Cl.[6] .......... B01D 63/00

[52] U.S. Cl. .......... 210/321.75; 210/321.6; 210/321.84; 210/456; 210/446; 210/443; 210/435; 604/406; 96/6; 96/7

[58] Field of Search .......... 210/321.6, 321.75, 210/321.84, 436, 446, 443, 435, 456, 645; 604/406; 95/43; 96/6, 7

[56] References Cited

U.S. PATENT DOCUMENTS

| | | | |
|---|---|---|---|
| 3,523,408 | 8/1970 | Rosenberg . | |
| 3,734,851 | 5/1973 | Matsumura | 210/321.75 |
| 3,803,810 | 4/1974 | Rosenberg . | |
| 3,854,907 | 12/1974 | Rising . | |
| 3,905,905 | 9/1975 | O'Leary et al. . | |
| 4,009,714 | 3/1977 | Hammer . | |
| 4,066,556 | 1/1978 | Vaillancourt . | |
| 4,151,088 | 4/1979 | Wolf, Jr. et al. | 210/321.75 |
| 4,177,149 | 12/1979 | Rosenberg . | |
| 4,190,426 | 2/1980 | Ruschke . | |
| 4,238,207 | 12/1980 | Ruschke . | |
| 4,276,170 | 6/1981 | Vaillancourt . | |
| 4,294,594 | 10/1981 | Sloane, Jr. et al. . | |
| 4,298,358 | 11/1981 | Ruschke . | |
| 4,326,957 | 4/1982 | Rosenberg . | |
| 4,341,538 | 7/1982 | Vadnay et al. . | |
| 4,343,705 | 8/1982 | Legg | 210/443 |
| 4,459,139 | 7/1984 | von Reis et al. . | |
| 4,525,182 | 6/1985 | Rising et al. . | |
| 4,534,757 | 8/1985 | Geller . | |
| 4,537,680 | 8/1985 | Barth . | |
| 4,568,366 | 2/1986 | Frederick et al. . | |
| 4,585,435 | 4/1986 | Vaillancourt | 604/27 |
| 4,786,474 | 11/1988 | Cooper | 210/321.75 |
| 4,906,260 | 3/1990 | Emheiser et al. . | |
| 4,923,620 | 5/1990 | Pall . | |
| 5,229,012 | 7/1993 | Pall et al. . | |
| 5,252,222 | 10/1993 | Matkovich et al. . | |
| 5,344,561 | 9/1994 | Pall et al. . | |
| 5,348,646 | 9/1994 | Costello, Jr. et al. . | |
| 5,439,587 | 8/1995 | Stankowski et al. . | |

FOREIGN PATENT DOCUMENTS

| | | |
|---|---|---|
| 2 000 685 | 1/1979 | United Kingdom . |
| 2 272 385 | 5/1994 | United Kingdom . |
| WO 95/06506 | 3/1995 | WIPO . |

OTHER PUBLICATIONS

Announcement by Arbor Technologies Inc. of an I.V. filter, one page, Jan. 1995.

Brochure entitled "Medical Filtration Devices for Health Care Equipment and Supply Manufacturers", pp. 1–4, 1987, published by Gelman Sciences.

Brochure entitled "Filtration Solutions for the Health Care Industry", 20 pages, 1993, published by Gelman Sciences.

*Primary Examiner*—Ana Fortuna

*Attorney, Agent, or Firm*—Steven P. Shurtz; Brinks Hofer Gilson & Lione

[57] ABSTRACT

An intravenous filter device comprises a filter housing having a front side, a back side, a first end, a second end, an inlet and an outlet, the housing containing a hydrophilic filtration media and defining a flow path such that intravenous fluid entering the housing through the inlet passes through the filtration media before passing out of the housing through the outlet. Inlet and outlet tubing connectors, both preferably attached to the front side of the filter housing, form, respectively, the housing inlet and outlet. In the preferred embodiment the connectors are raised above the front side or the housing such that tubing connected to the connectors does not intersect the front side of the housing. At least one vent hole in the housing provides a passageway for gas to escape from the housing, the vent hole being preferably open to the front side of the housing. A hydrophobic membrane is positioned between the vent hole and the flow path at a position along the flow path between the inlet and the hydrophilic filtration media. In a preferred embodiment, a tubing clip is provided to help orient the filter to make it self priming and prevent I.V. set tubing from kinking,

23 Claims, 3 Drawing Sheets

16
50
52
52
60
10
20
28
18

16
50
52
52
60
20
18
45
40
30
28

INTRAVENOUS FILTER DEVICE

BACKGROUND OF THE INVENTION

This invention pertains to the field of membrane-type filter devices, particularly intravenous filter devices which employ both hydrophilic and hydrophobic membranes.

This invention relates broadly to membrane-type filter devices, and especially to filter devices used to remove impurities from liquids or fluids that are to be introduced intravenously to the human body. Some fluids useful with this invention include saline solutions and nutrient solutions, or other solutions that act as carriers for drugs. Other fluids useful with this invention are not listed but are well known to those having ordinary skill in the art.

One of the problems encountered with conventional membrane-type intravenous filter devices is the presence of gas. The fluid must be filtered before entering the patient in order to remove gas bubbles and contaminants. Gas in the housing or mixed with the liquid tends to prevent effective filtration of the liquid. When the filter is first attached to the patient and fluid flow is initiated, air frequently enters the lines or is already present in the filter device. A wetted hydrophilic membrane filter will generally not allow the air to pass. Thus, entrapped air tends to prevent fluid from entering the patient, It is therefore desirable to remove this entrapped air as quickly and continuously as possible. This is often referred to as priming the filter.

Several devices are available to remove air from membrane-type filter devices. These devices make use of hydrophobic membranes which are capable of passing air out of the filter housing through vents, but liquids will not pass through the membranes. Conventional intravenous filters employ this principle but have some shortcomings. For example, several commercial devices are not altogether satisfactory because they do not remove air through the outlet port in the short time that is necessary, or they require the filter to be turned upside down, or in an orientation different than how the filter will be used, during priming. This can lead to confusion and a lack of proper priming, leaving gas entrapped in areas of the housing that are not contiguous to the hydrophobic membrane.

Various devices have attempted to correct these shortcomings. Some utilize rectangular filters to assist self-priming, with an inlet at the bottom and an outlet at the top or the filter. Such devices must be tilted from a horizontal plane in order to be self-priming. Some do not utilize a hydrophobic-type filter medium. Still other filter units employ a combination of hydrophilic and hydrophobic filters arranged side-by-side in alternate sequence. A disadvantage, however, is that this configuration provides a hydrophobic zone on each end of the housing. Although these chambers appear to provide for the escape of entrapped air, they also create a zone where liquids can gather and be incapable of passing through either the hydrophilic membrane or the hydrophobic membrane. Further, drugs in intravenous fluids often have different densities than other fluids administered to the patient. This may mean that the drugs will be in a portion of the filter adjacent a hydrophobic membrane if the filter unit is in a vertical position. When this is the case, the drugs may not immediately be administered to the patient. This could conceivably cause problems, especially if drugs must be administered quickly to the patient.

Additionally, there are increased manufacturing costs from having to seal two hydrophobic membranes while constructing the filter, plus this doubles the possibility of a defective filter due to a leak if the hydrophobic material is not correctly sealed.

Another common problem is that, when filters are taped to a patient's arm, or to a support surface to immobilize the tubing connection to the filter, the tape blocks the vents, preventing gas in contact with the hydrophobic membranes from passing out of the filter housing.

In other devices, the filter does not have a flat face on which the filter can be placed to easily secure it to a flat surface, or the vent or vents are on a flat face so that if someone does tape the filter to a flat surface the vents are blocked.

Another problem is that support ribs, used to hold the filtration media away from the wall of the filter housing, create many small flow channels, Small bubbles can form in these channels during priming and, even though the filter is properly oriented, the bubbles may stay trapped in the narrow ends of the channels and not be flushed out the outlet port.

An additional problem is that many filters having tubing connections that orient the filter in such a manner that if the filter is suspended from an intravenous fluid source, with additional tubing suspended therefrom, the filter either does not hang so that the vent is properly positioned, or the weight of the filter causes the filter to tip to one side and kink the tubing.

The problems enumerated in the foregoing are not intended to be exhaustive but rather are among many which tend to impair the effectiveness of previously known filter devices. Other noteworthy problems -may also exist; however, those presented above should be sufficient to demonstrate that filter devices appearing in the art are not altogether satisfactory.

SUMMARY OF THE INVENTION

This invention is based on the discovery of a continuously venting, self-priming filter device. Although the filter device of the present invention may be used for filtering a wide variety of fluids, its main usefulness is for medical and diagnostic purposes, i.e, intravenous filter devices. This is because quick self-priming and continuous venting is particularly important for intravenous applications. A surprising advantage of this invention is that the shape of the filter, in conjunction with the location of the tubing connectors, tubing clip and the vent, assists the filter device in quickly purging air during priming while the filter is in the position of its intended use and continuously venting gases entrapped in the chamber during use.

In one aspect, the invention comprises an intravenous filter device comprising a filter housing having a front side, a back side, a first end, a second end, an inlet and an outlet, the housing containing a hydrophilic filtration media and defining a flow path such that intravenous fluid entering the housing through the inlet passes through the filtration media before passing out of the housing through the outlet; inlet and outlet tubing connectors, both attached to the front side of the filter housing and forming, respectively, the housing inlet and outlet, the connectors being raised above the front side or the housing such that tubing connected to the connectors does not intersect the front side of the housing; at least one vent hole providing a passageway for gas to escape from the housing, the at least one vent hole being open to the front side of the housing; and a hydrophobic membrane positioned between the at least one vent hole and the flow path at a position along the flow path between the inlet and the hydrophilic filtration media.

In another aspect, the invention comprises a filter housing having a front side, a back side, a first end, a second end, an inlet and an outlet, the housing containing a hydrophilic filtration media and defining a flow path such that intravenous fluid entering the housing through the inlet passes through the filtration media before passing out of the housing through the outlet; inlet and outlet tubing connectors both attached to the front side of the filter housing and forming, respectively, the inlet and outlet; a plurality of vent holes adjacent the first end of the filter housing providing passageways for gas to escape from the housing; a hydrophobic membrane positioned between the vent holes and the flow path; and a tubing clip attached to the housing, the positions of the tubing connectors and the tubing clip being such that when the inlet of the device is attached to tubing suspended from an intravenous fluid source and the outlet is connected to tubing suspended from the filter device, and the tubing clip is attached to said tubing, the vent holes are positioned such that gas bubbles entering the filter housing through the inlet will rise within the housing and contact the hydrophobic membrane and pass out one or more of the vent hole.

The filter of the present invention is vented and self priming. In the preferred embodiment the vents are located adjacent the tubing connectors, and the tubing connectors extend outwardly of the front side of the device to such an extent that they prevent the vent holes from being blocked by tape used to secure the filter to a support. In the preferred embodiment, the tubing clip and tubing connectors are positioned and aligned so that, when suspended in an I.V. set, the filter and tubing hang straight without any tendency to kink and the vents are located near the top of the filter. Also, the preferred embodiment vent, inlet and outlet locations provide that the filter can be primed with the filter in the same orientation in which it is intended to be used.

These and other advantages of the invention, as well as the invention itself, will be better understood in view of the accompanying drawings.

DETAILED DESCRIPTION OF THE DRAWINGS AND AN EMBODIMENT OF THE INVENTION

Figure 1:
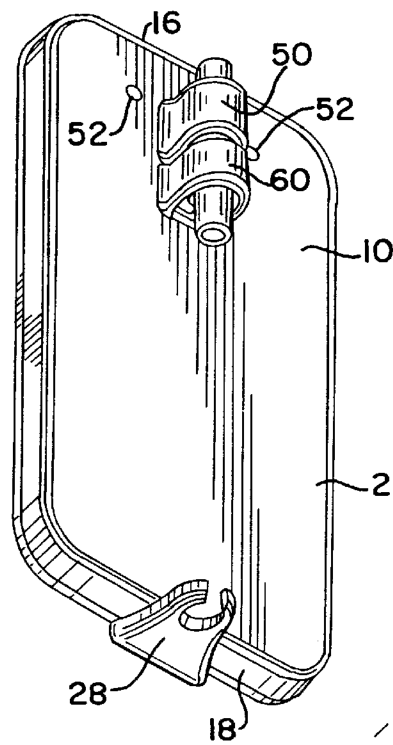
FIG. 1 is a perspective view of a preferred filter unit in accordance with the present invention.
Figure 2:
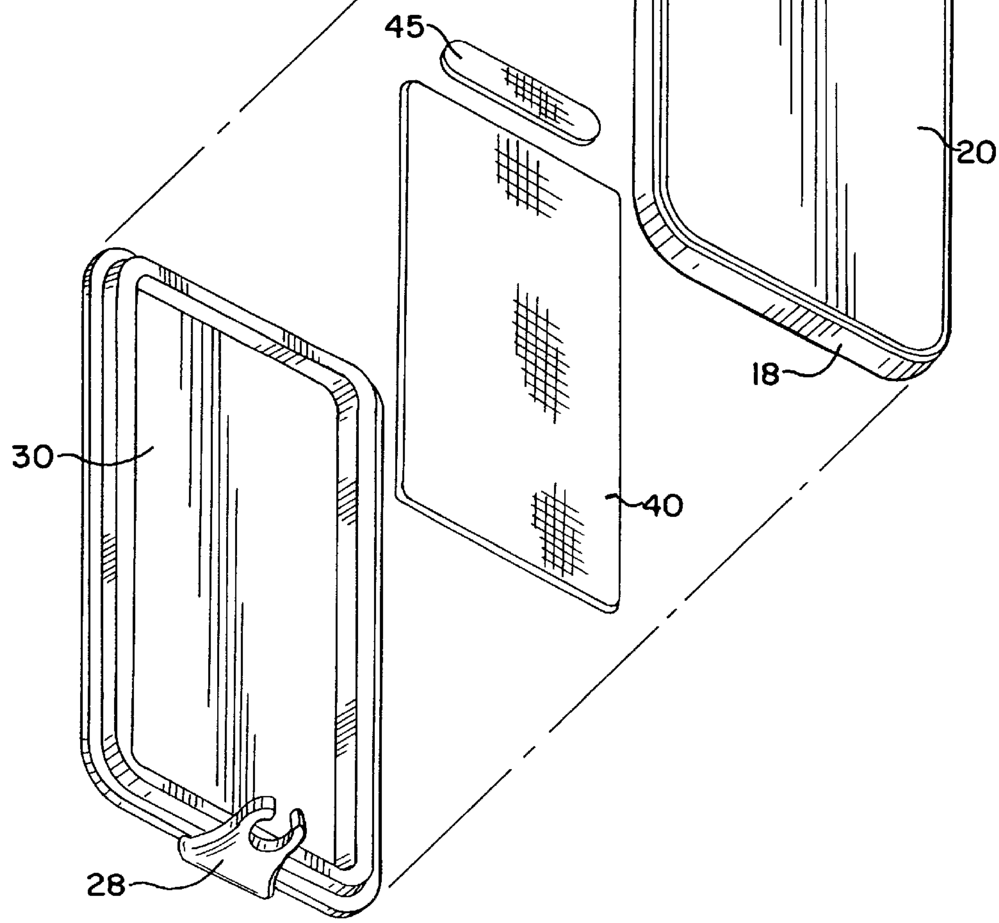
FIG. 2 is an exploded view of the components making up the filter of FIG. 1.
Figure 3:
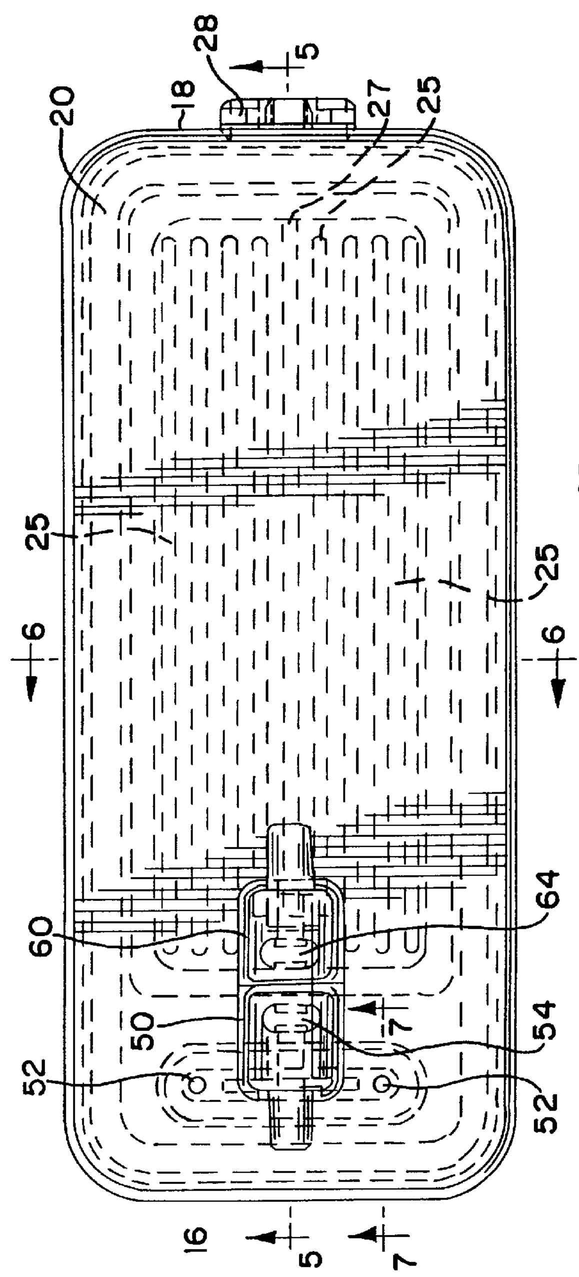
FIG. 3 is a plan view of the front side of the filter of FIG. 1.
Figure 4:
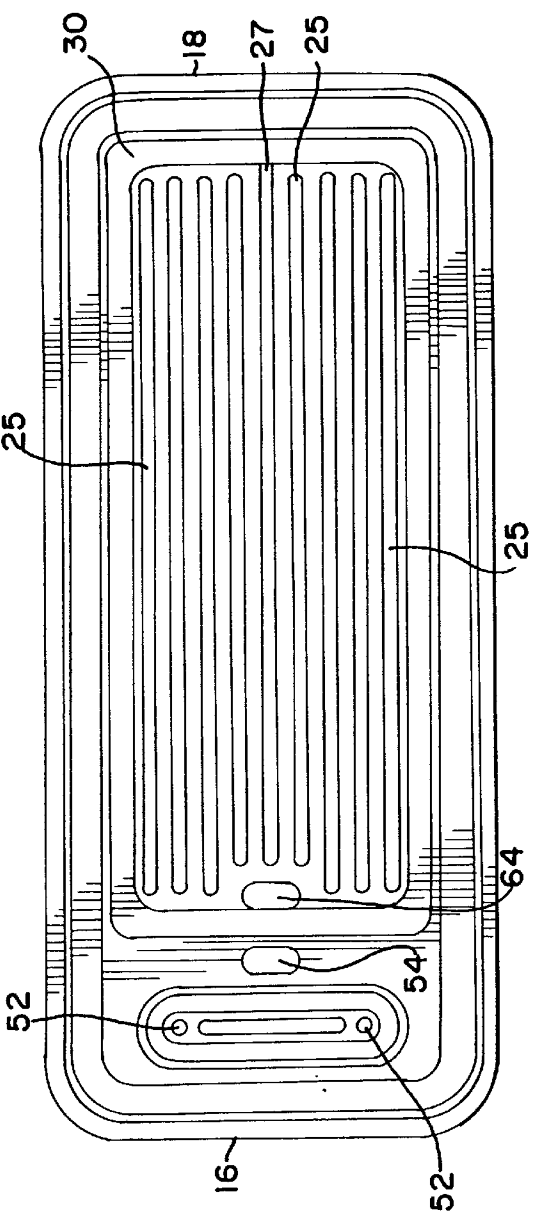
FIG. 4 is a plan view of the back side of the filter of FIG. 1.
Figure 7:
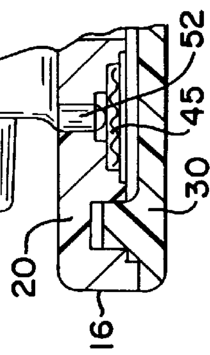
FIG. 7 is a cross-sectional view taken along line 7—7 of FIG. 3.

FIGS. 1–7 show a new, improved self-priming intravenous filter unit in accordance with the present invention. This particular unit, which is the preferred embodiment, comprises a substantially flat housing 10 which comprises an inlet chamber 12 and an outlet chamber 14 separated by a hydrophilic filtration media 40 (FIG. 7). This filter comprises a front housing half or part 20 and a back half or part 30, a hydrophilic filtration media 40 and a hydrophobic vent membrane 45 (FIG. 2).

Figure 5:
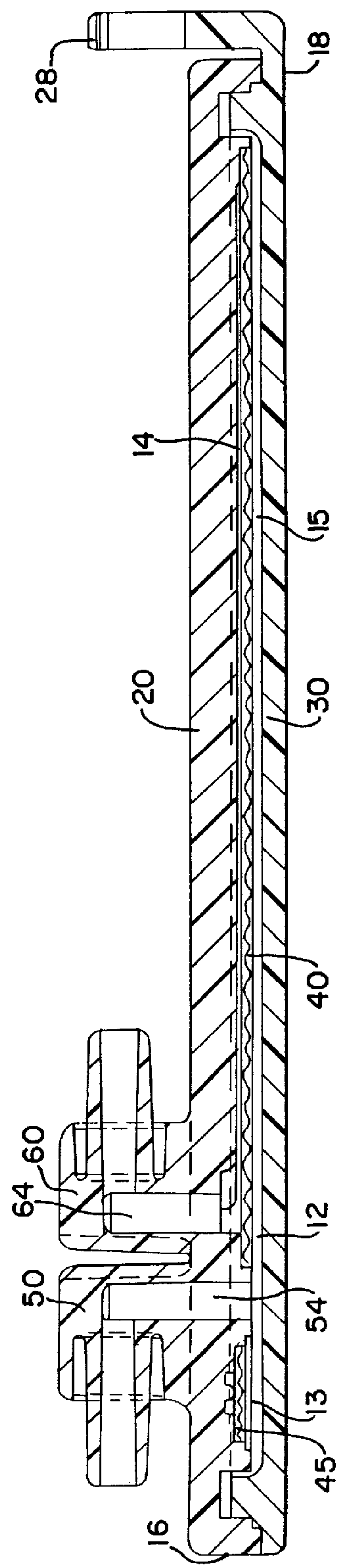
FIG. 5 is a cross-sectional view taken along line 5—5 of FIG. 3.
Figure 6:
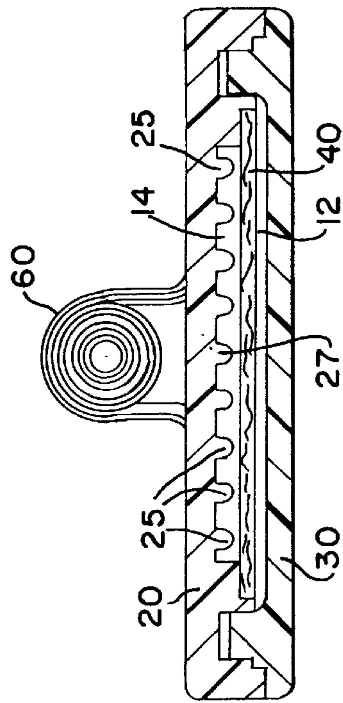
FIG. 6 is a cross-sectional view taken along line 6—6 of FIG. 3.

The location or the hydrophilic filtration media 40 between the two chambers is seen more easily in FIGS. 5 and 6. AS Can be seen in FIG. 5, the two chambers are separated lengthwise by the hydrophilic filtration media 40. Preferably, the housing 10 is transparent and the corners of the housing are rectangular. An inlet to the housing delivers fluid to the inlet chamber, An outlet delivers fluid from the outlet chamber after the fluid has passed through the media 40. The device also comprises vent holes 52 for releasing entrapped gas from the first chamber.

The inlet to the housing 10 comprises an inlet tubing connector 50. An outlet tubing connector 60 comprises the outlet of the housing 10. As shown in FIGS. 1, 2, 3 and 5, preferably the inlet and outlet tubing connectors 50,60 are placed back-to-back with respect to each other, with the inlet tubing connector facing the first or top end 16 of the housing and the outlet tubing connector 60 facing the second or bottom end 18 of the housing. The inlet and outlet connectors 50,60 are preferably located adjacent the first end 16 of the housing 10, and are spaced inwardly of the housing ends.

Preferably the connectors 50,60 are raised above the surface of front side of the housing 10 such that tubing connected to the connectors does not intersect the front side of the housing 10. For male tubing connectors, as shown, this means that tubing connected to the connectors will fit onto the connectors without any substantial interference with the surface of the front side of the housing. If female connectors were used, instead of the male connection shown, this means that the bottom of the inside connecting surface would be above the plane of the filter housing front side. By having the tubing connectors raised to such a substantial height, the profile or the front side of the filter housing 10 is such that it will not be mistakenly placed against the arm of a patient. Instead, the back side of the filter housing 10, which in flat, will be placed against the patient's arm or other support surface. With the vents 52 on the front side, this prevents the vents from being inadvertently blocked, which is possible with filters having low profile connectors which may inadvertently be taped to a patient's arm with the vents against the skin.

The preferred filter housing 10 is symmetrical about a plane that is perpendicular to the back side of the housing and intersects the tubing connectors 50,60. Also, the tubing connectors are preferably in line with one another. The preferred filter housing 10 includes a tubing clip 28 attached to the filter housing, preferably at the second, or bottom end 18. The clip 28 is also preferably in line with the tubing connectors 50,60. In this regard, the filter is then evenly balanced side to side so that when the filter is suspended from a intravenous fluid source, the filter hangs straight up and down and does not cause kinks in the tubing.

The tubing clip 28 helps to keep this straight alignment, and also helps to assure that the filter is correctly positioned so that gas bubbles entering the filter will rise within the housing 10 and contract the hydrophobic membrane 45 and pass out through the vent holes 52, located adjacent the first or top end 16 of the filter housing 10.

Preferably there are two vent holes 52, although only one vent hole is required, and more may be used. In the preferred embodiment, the vent holes are open to the front side of the filter housing 10. Also, in the preferred embodiment, both vent holes 52 are in direct communication with a single hydrophobic membrane member 45, which has an elongated oval shape as shown in FIG. 2.

As best seen in FIG. 5, fluid enters the filter housing 10 through inlet tubing connector 50. An inlet channel 54 allows the fluid to pass to the inlet chamber 12 which is located adjacent the back side of the filter housing 10. The inlet chamber 12 has two portions, a first, or top portion 13, adjacent the hydrophobic membrane 45, and a second, or bottom portion 15 adjacent the hydrophilic filtration media 40. The inlet channel 54 delivers fluid into the chamber 12 at a point in between portion 13 and 15. When the housing is upright, or on an inclined surface with the first end 16 higher than the second end 18, gas bubbles entering the chamber 12 will rise into portion 13 and contact the hydrophobic membrane 45 and exit vents 52. When the filter is supported on a level surface, a gas bubble may grow around the base of channel 54 until it is large enough to contact the hydrophobic membrane 45. In either event, fluid will be able to reach the hydrophilic filtration media 40 and pass therethrough. Because of the location of the inlet channel 54 between the two portions of the inlet chamber, it is believed that only one hydrophobic vent membrane will be necessary for proper operation of the filter, thus simplifying production and reducing the possibility of leaks which can occur when vent materials are not properly sealed.

After passing through hydrophilic filtration media 40, fluid enters outlet chamber 14 and is directed towards outlet tubing connector 60. The connector 60 is preferably at the top of outlet chamber 14 when the filter is oriented as shown in FIG. 1. In this orientation, the filter is self priming as any gas in the outlet chamber will rise as fluid enters the outlet chamber through filtration media 40.

The flow path downstream of the filtration media 40 preferably includes flow channels created by a plurality of ridges 25 molded onto the inside of the front housing part 20. The ridges 25 support the filtration media 40 against pressure exerted by the fluid trying to pass through the media 40. The ridges 25 run In a direction from the second end 18 of the housing 10 toward the outlet channel 64 in outlet tubing connector 60, At least some of the ridges 25, and preferably all but one, center ridge 27, terminate short of the second end 18 of the housing so that fluid can flow around the bottom ends of the ridges 25. This prevents small bubbles from forming in the bottom of the channels between ridge 25. The center ridge 27 does connect to the second end 18 of the housing so as to help evenly distribute the flow between the two sides of the chamber 14.

The methods and essential materials for making the housing 10 are well known in the art and generally involve the use of clear synthetic resins. The overall size of the housing 10 is generally well known and is not substantially different from conventional intravenous filter devices. The preferred device, shown in FIGS. 1–7 should have a void volume of less than about 6 ml and preferably has a void volume of less than about 3 ml. Generally speaking, for intravenous applications, smaller filters are preferred over lager filters. A smaller filter is lighter and more convenient for the patient. Furthermore, the low void volume of a smaller filter means there is a smaller hold-up volume than with a larger filter; that is, there is less liquid remaining in the filter device at any given time. Low hold-up volume in intravenous filters is especially preferred for low administration rates. Low void volume also helps the filter prime more quickly.

The filter housing 10 could also be constructed of flexible material such as polypropylene, polyethylene or polyvinyl chloride. However, because visibility is desirable, the preferred embodiment is made from a substantially transparent material. A transparent filter provides visibility such that the fluid to be filtered can be readily seen by the patient, doctor or medical attendant, Thus, a gas bubble, foreign object or liquid contaminant blocking a portion or the hydrophilic membrane can be readily detected. Accordingly, a preferred material is an impact-modified acrylic such as acrylonitrile butadiene styrene terpolymer or any other plastic material that is durable, transparent and not unduly brittle. Materials such as polypropylene and polyethylene are less transparent and thus normally less preferred. However, a less transparent but more durable material may be preferred if high fluid pressures are to be employed.

The housing 10 of the present invention can be made by sealing the two housing parts 20 and 30 together to form a cavity. The housing parts 20, 30 are sealed by conventional techniques. Any workable method of sealing the device against leakage is contemplated, including radio frequency weld sealing, hot melt sealing, ultrasonic sealing or solvent sealing. Although several methods of sealing are within the scope of the invention, it has been found that ultrasonic weld sealing is preferred for acrylic materials, In this embodiment, each housing half 20, 30 has a flange about its rim that fits to the flange of the other housing half. Before the two halves 20, 30 are sealed together, the hydrophilic filtration media 40 is beat sealed to the front housing half 20. The hydrophobic vent material 45 is also sealed to cover the opening to vent holes 52 before the housing parts are assembled. A heated die is used to seal these materials to the front housing part 20.

The hydrophilic filtration media 40 and hydrophobic membrane 45 of the prevent invention are well known in the art. The preferred material for the hydrophobic membrane 45 is a polyester-supported PTFE having PTFE membrane attached to a polyester fibrous pad by a polyester adhesive. The preferred membrane 45 is manufactured by W. L. Gore & Associates, Elkton, Md., having a 0.02 micron pore size. A preferred material for the media 40 is polysulfone, but the media 40 can also be made of a PVC acrylic copolymer, polyvialinadifluoride, cellulose, nylon or polyamide. The hydrophilic media 40 is microporous, and the mean pore size of the media is from about 0.2 micron to about 150 microns. The most preferred mean pore size is about 0.22 micron, The media 40 is shaped to fit the housing 10, being large enough for its edges to be sealed to be substantially leakproof. The media 40 surface area of the presently preferred embodiment is about 9 square centimeters. The preferred embodiment utilizes the smallest surface area possible so that a more economical unit can be produced at a reduced cost. For a unit having a hydrophilic media 40 surface area of about 9 square centimeters, the unit has a preferred flow rate range of from less than about 25 ml to about 50 ml per minute at 1 psig. The operating fluid pressure range is from about 1 psig to about 5 psig.

Although the preferred housing lo is flat, the shape is not critical. Although in this embodiment, the corners are bevelled, they may also be rounded, depending on aesthetic preference, desired shape and economics in molding. Such non-rectangular corners reduce the tendency of gas bubbles to occupy the corners of the chamber and avoid the hydrophobic membranes 45 of the vent holes 52.

By having the inlet connector 50 and outlet connector 60 in a back-to-back relationship, the inlet and outlet channels 54 and 64 can be close together, Preferably the connectors 50 and 6O are only a millimeter or so apart, and may be molded as one monolithic member.

By having the inlet connector 50, outlet connector 60 and tubing clip all attached to the front housing part 20, the back housing part 30 has a fairly simple design and can be easily molded. The front housing part 20 is preferably molded with the connectors 50,60 and tubing clip 28 all in one mold, though other methods of attaching these items could be used.

The preferred embodiment incorporates many features, not all of which are necessary for achieving some of the benefits of the present invention. Also, while a preferred embodiment or me filter has been shown, many variations are possible. For example, support ribs could be provided on the back housing part 30 to support the filtration media 40 against back pressure when the filter is to be used on devices that produce a back pressure.

It should be appreciated that the products of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. An intravenous filter device comprising:

a) a filter housing having a front side, a back side, a first end, a second end, an inlet and an outlet, the housing containing a hydrophilic filtration media and defining a flow path such that intravenous fluid entering the housing through the inlet passes through the filtration media before passing out of the housing through the outlet;

b) inlet and outlet tubing connectors, both attached to the front side of the filter housing adjacent the first end thereof and forming, respectively, the housing inlet and outlet, the connectors being raised above the front side of the housing and placed back-to-back with respect to each other, with the connectors being in line with one another and facing in opposite directions away from one another;

c) at least one vent hole providing a passageway for gas to escape from the housing, the at least one vent hole being open to the front side of the housing, and;

d) a hydrophobic membrane positioned between the at least one vent hole and the flow path at a position along the flow path between the inlet and the hydrophilic filtration media.

2. The intravenous filter device of claim 1 further comprising a tubing clip attached to the filter housing.

3. The intravenous filter device of claim 2 wherein the tubing clip is located at the second end of the filter.

4. The intravenous filter device of claim 1 wherein a plurality of vent holes are provided, each being open to the front side of the housing.

5. The intravenous filter device of claim 4 wherein at least two of said vent holes are in direct communication with a single hydrophobic membrane.

6. The intravenous filter device of claim 1 wherein the at least one vent hole is positioned adjacent one or the tubing connectors closely enough so that tape used to secure the filter device to a support will not block the vent hole.

7. The intravenous filter device of claim 1 wherein the front and back sides are generally rectangular.

8. The intravenous filter device of claim 1 wherein the housing comprises an inlet chamber adjacent the back side of the housing.

9. The intravenous filter device of claim 8 wherein the inlet chamber comprises a first portion and a second portion, with the inlet connecting to the inlet chamber between the first and second portions.

10. The intravenous filter device of claim 9 wherein the first portion of the inlet chamber is adjacent to the hydrophobic membrane and the second portion of the inlet chamber is adjacent to the hydrophilic filtration media.

11. The intravenous filter device of claim 1 wherein the housing is symmetrical about a plane that is perpendicular to the back side of the housing and intersects the inlet and outlet tubing connectors.

12. The intravenous filter device of claim 1 wherein the back side of the filter housing is generally flat.

13. The intravenous filter device of claim 1 wherein the tubing connectors are spaced inwardly with respect to the first and second ends of the housing.

14. The intravenous filter device of claim 1 wherein the device has only one hydrophobic membrane.

15. The intravenous filter device of claim 1 wherein the at least one vent hole is also adjacent the first end of the housing.

16. An intravenous filter device comprising:

a) a filter housing having a front side, a back side, a first end, a second end, an inlet and an outlet, the housing containing a hydrophilic filtration media and defining a flow path such that intravenous fluid entering the housing through the inlet passes through the filtration media before passing out of the housing through the outlet;

b) inlet and outlet tubing connectors both attached to the front side of the filter housing and forming, respectively, the inlet and outlet, the inlet tubing connector being located adjacent the first end of the housing, and the tubing connections being placed back-to-back with respect to each other, with the connectors being in line with one another and facing in opposite directions away from one another;

c) a plurality of vent holes adjacent the first end of the filter housing providing passageways for gas to scape form the housing;

d) a hydrophobic membrane positioned between the vent holes and the flow path; and e) a tubing clip attached to the housing, the positions of the tubing connectors and the tubing clip being such that when the inlet of the device is attached to a tubing suspended from an intravenous fluid source and the outlet is connected to a tubing suspended from the filter device, and the tubing clip is attached to said tubing suspended from the filter device the vent holes are positioned such that gas bubbles entering the filter housing through the inlet will rise within the housing and contact the hydrophobic membrane and pass out one or more of the vent holes.

17. The intravenous filter device of claim 16 wherein the clip is located adjacent the second end of the housing.

18. The intravenous filter device of claim 16 wherein the filter housing is made of joined thermoplastic housing parts and the tubing clip and tubing connectors are molded as part of the housing part to which they are attached.

19. The intravenous filter device of claim 18 wherein both tubing connectors and tubing clip are molded on the same housing part.

20. The intravenous filter device of claim 16 wherein the tubing connectors are in line with the tubing clip.

21. The intravenous filter device of claim 16 wherein the flow path downstream of the hydrophilic filtration media includes flow channels created by a plurality of ridges running in a direction from the second end of said housing toward said outlet.

22. The intravenous filter device of claim 21 wherein at least some of said ridges terminate short of said second end or said housing.

23. The intravenous filter device of claim 22 wherein at least one of said ridges connects to the second end of said housing.

* * * * *

UNITED STATES PATENT AND TRADEMARK OFFICE

CERTIFICATE OF CORRECTION

PATENT NO. : 5,827,429
DATED : October 27, 1998
INVENTOR(S) : R. R. Ruschke et al.

It is certified that error appears in the above-identified patent and that said Letters Patent is hereby corrected as shown below:

Title page, Column 2,
ABSTRACT,
Line 11, delete "or" after "side" and substitute -- of -- in its place.

Claim 6,
Line 2, delete "or" before "the" and substitute -- of -- in its place.

Claim 16,
Line 13, delete "connections" and substitute -- connectors -- in its place.
Lines 18-19, delete "scape form" and substitute -- escape from -- in its place.
Line 28, immediately after "device" insert -- , -- (comma).

Signed and Sealed this

Fifth Day of March, 2002

*Attest:*

JAMES E. ROGAN

*Attesting Officer*

*Director of the United States Patent and Trademark Office*